US008785188B2

(12) United States Patent
Har-Noy

(10) Patent No.: US 8,785,188 B2
(45) Date of Patent: *Jul. 22, 2014

(54) METHOD TO FORMULATE T-CELLS

(75) Inventor: Michael Har-Noy, Jerusalem (IL)

(73) Assignee: Immunovative Therapies, Ltd., Jerusalem (IL)

(*) Notice: Subject to any disclaimer, the term of this patent is extended or adjusted under 35 U.S.C. 154(b) by 974 days.

This patent is subject to a terminal disclaimer.

(21) Appl. No.: 12/887,039

(22) Filed: Sep. 21, 2010

(65) Prior Publication Data

US 2011/0028912 A1 Feb. 3, 2011

Related U.S. Application Data

(60) Continuation of application No. 12/173,330, filed on Jul. 15, 2008, now Pat. No. 8,076,135, which is a division of application No. 11/069,010, filed on Mar. 1, 2005, now Pat. No. 7,402,431, and a continuation-in-part of application No. 10/838,454, filed on May 4, 2004, now Pat. No. 7,435,592.

(60) Provisional application No. 60/549,032, filed on Mar. 1, 2004, provisional application No. 60/547,966, filed on Feb. 26, 2004, provisional application No. 60/545,450, filed on Feb. 18, 2004, provisional application No. 60/470,171, filed on May 13, 2003.

(51) Int. Cl.
*C12N 5/00* (2006.01)
*C12N 5/02* (2006.01)
*C12N 5/0783* (2010.01)
*A61K 39/00* (2006.01)

(52) U.S. Cl.
CPC .......... *C12N 5/0636* (2013.01); *C12N 2531/00* (2013.01); *A61K 2039/57* (2013.01); *A61K 2039/5154* (2013.01); *C12N 2501/515* (2013.01); *C12N 2533/40* (2013.01); *C12N 2501/51* (2013.01)
USPC .......................................... 435/372; 435/377

(58) Field of Classification Search
None
See application file for complete search history.

(56) References Cited

U.S. PATENT DOCUMENTS

| | | |
|---|---|---|
| 5,806,529 A | 9/1998 | Reisner et al. |
| 6,352,694 B1 | 3/2002 | June et al. |
| 6,534,055 B1 | 3/2003 | June et al. |
| 6,905,680 B2 | 6/2005 | June et al. |
| 6,905,874 B2 | 6/2005 | Berenson et al. |
| 2002/0115214 A1 | 8/2002 | June et al. |
| 2002/0127208 A1 | 9/2002 | Waller et al. |
| 2004/0228848 A1 | 11/2004 | Har-Noy |

FOREIGN PATENT DOCUMENTS

| | | |
|---|---|---|
| WO | 94/12196 A1 | 6/1994 |
| WO | 03/024989 A2 | 3/2003 |
| WO | 03/038062 A2 | 5/2003 |
| WO | 03/057171 A2 | 7/2003 |
| WO | 2005/001074 A1 | 1/2005 |
| WO | 2005/081982 A2 | 9/2005 |

OTHER PUBLICATIONS

Yashiro-Ohtani, Y. et al. (2000). "Non-CD28 Costimulatory Molecules Present in T Cell Rafts Induce T Cell Costimulation by Enhancing the Association of TCR with Rafts." The Journal of Immunology, vol. 164, No. 3: pp. 1251-1259.
Yoon, T. J. et al. (1998). "Prophylactic effect of Korean mistletoe (Viscum album coloratum) extract on tumor metastasis is mediated by enhancement of NK cell activity." International Journal of Immunopharmacology, Vo. 20, No. 4-5: pp. 163-172.
Zitvogel, L. et al. (1996). "Therapy of Murine Tumors with Tumor Peptide-Pulsed Dendritic Cells: Dependence on T Cells, B7 Costimulation, and T Helper Cell 1-associated Cytokines." Journal of Experimentive Medicine, vol. 183, No. 1: pp. 87-97.
Anderson, P. et al. (1988). "Crosslinking CD3 with CD2 Using Sepharose-Immobilized Antibodies Enhances T Lymphocyte Proliferation." Cellular Immunology, vol. 115, No. 2: pp. 246-256.
Antin, J. H. et al. (1992). "Cytokine Dysregulation and Acute Graft-Versus-Host Disease." Blood, vol. 80, No. 12: pp. 2964-2968.
Asselin-Paturel et al. (1998). "Quantitative Analysis of Th1, Th2 and TGF-β1 Cytokine Expression in Tumor, TIL and PBL of Non-Small Cell Lung Cancer Patients." Int. J. Cancer, vol. 77, No. 1: pp. 7-12.
Bachmann, M. F. et al. (1997). "Distinct Roles for LFA-1 and CD28 During Activation of Naive T Cells: Adhesion Versus Costimulation," Immunity, vol. 7, No. 4: pp. 549-557.
Banu, N. et al. (1999). "TGF-β1 down-regulates induced expression of both class II MHC and B7-1 on primary murine renal tubular epithelial cells." Kidney International, vol. 56, No. 3: pp. 985-994.
Baroja, M.L. et al. (1989). "The Anti-T Cell Monoclonal Antibody 9.3 (Anti-CD28) Provides a Helper Signal and Bypasses the Need for Accessory Cells in T Cell Activation with Immobilized Anti-CD3 and Mitogens." Cellular Immunology, vol. 120, No. 1: pp. 205-217.
Baxevanis, C. N. et al. (2000). "Compromised anti-tumor responses in tumor necrosis factor-α knockout mice." Eur. J. Immunol., vol. 30, No. 7: pp. 1957-1966.
Belardelli, F. et al. (2002). "Cytokines as a link between innate and adaptive antitumor immunity." Trends in Immunology, vol. 23 No. 4: pp. 201-208.

(Continued)

*Primary Examiner* — Michail Belyavskyi
(74) *Attorney, Agent, or Firm* — Westman, Champlin & Koehler, P.A.; Z. Peter Sawicki; Visala Goswitz

(57) ABSTRACT

A method for formulating T-cells for use as a medicant comprises activating the T-cells by incubating the T-cells in a nutrient culture media with an activating agent. The T-cells together with the activating agent are suspended in a media suitable for infusion. The activated T-cells are packaged together with the activating agent in a container suitable for administration to a patient.

4 Claims, No Drawings

(56) References Cited

OTHER PUBLICATIONS

Blazar, B. R. et al. (1997). "Recent advances in graft-versus-host disease (GVHD) prevention." Immunological Reviews, vol. 157: pp. 79-109.

Blazar, B. R. et al. (1998). "Rapamycin Inhibits the Generation of Graft-Versus-Host Disease- and Graft-Versus-Leukemia-Causing T Cells by Interfering with the Production of Th1 or Tc1 Cytotoxic Cytokines." Journal of Immunology, vol. 160, No. 11: pp. 5355-5365.

Carayol, G. et al. (1997). "Quantitative Analysis of T Helper 1, T Helper 2, and Inflammatory Cytokine Expression in Patients After Allogeneic Bone Narrow Transplantation: Relationship with the Occurrence of Acute Graft-Versus-Host Disease." Transplantation, vol. 63, No. 9: pp. 1307-1313.

Carpentier, A. F., G. Auf, et al. (2003). "CpG-oligonucleotides for cancer immunotherapy : review of the literature and potential applications in malignant glioma." Front Biosci 8: E115-27.

Chambers, C. A. et al. (1999). "Costimulatory regulation of T cell function." Current Opinion in Cell Biology, vol. 11, No. 2: pp. 203-210.

Champlin, R., I. Khouri, et al. (1999). "Allogeneic hematopoietic transplantation as adoptive immunotherapy. Induction of graft-versus-malignancy as primary therapy." Hematol Oncol Clin North Am 13(5): 1041-57, vii-viii.

Champlin, R., K. van Besien, et al. (2000). "Allogeneic hematopoietic transplantation for chronic lymphocytic leukemia and lymphoma: potential for nonablative preparative regimens." Curr Oncol Rep 2(2): 182-91.

Chang, J. W., M. Peng, et al. (2000). "Induction of Th1 response by dendritic cells pulsed with autologous melanoma apoptotic bodies." Anticancer Res 20(3A): 1329-36.

Chen, Q. et al. (1994). "Production of IL-10 by Melanoma Cells: Examination of its Role in Immunosuppression Mediated by Melanoma." Int. J. Cancer, vol. 56, No. 5: pp. 755-760.

Childs, R. et al. (2002). "Nonmyeloablative Stem Cell Transplantation for Solid Tumors: Expanding the Application of Allogeneic Immunotherapy." Seminars in Hematology, vol. 39, No. 1: pp. 63-71.

Childs, R. et al. (2000). "Regression of metastatic renal-cell carcinoma after nonmyeloablative allogeneic peripheral-blood stem-cell transplantation." The New England Journal of Medicine, vol. 343, No. 11: pp. 750-758.

Childs, R. W. (2000). "Nonmyeloablative allogeneic peripheral blood stem-cell transplantation as immunotherapy for malignant diseases." Cancer J 6(3): 179-87.

Childs, R. W. (2002). "Immunotherapy of solid tumors: nonmyeloablative allogeneic stem cell transplantation." MedGenMed 4(3): 13.

Cierici, M. et al. (1993). "A TH1→TH2 switch is a critical step in the etiology of HIV infection." Immunology Today, vol. 14, No. 3: pp. 107-111.

Cohen, P. A., L. Peng, et al. (2000). "CD4+ T cells in adoptive immunotherapy and the indirect mechanism of tumor rejection." Crit Rev Immunol 20(1): 17-56.

Damle, N. K. et al. (1989). "Stimulation Via the CD3 and CD28 Molecules Induces Responsiveness to IL-4 in CD4+GD29+CD45R- Memory T Lymphocytes." The Journal of Immunology, vol. 143, No. 6: pp. 1761-1767.

Das, H., S. Imato, et al. (2001). "Kinetic analysis of cytokine gene expression in patients with GVHD after donor lymphocyte infusion." Bone Marrow Transplant 27(4): 373-80.

Daubener, W. et al. (1995). "Establishment of T-helper type 1- and T-helper type 2-like human Toxoplasma antigen-specific T-cell clones." Immunology, vol. 86, No. 1: pp. 79-84.

Deeths, M. J. et al. (1999). "CD8+ T Cells Become Nonresponsive (Anergic) Following Activation in the Presence of costimulation." The Journal of Immunology, vol. 163, No. 1: pp. 102-110.

De Vita, F., M. Orditura, et al. (2000). "Serum interleukin-10 is an independent prognostic factor in advanced solid tumors." Oncol Rep 7(2): 357-61.

de Waal Malefyt, R. et al. (1993). "Direct Effects of IL-10 on Subsets of Human CD4+ T Cell Clones and Resting T Cells. Specific Inhibition of IL-2 Production and Proliferation." The Journal of Immunology, vol. 150, No. 11: pp. 4754-4765.

D'Orazio, T. J. et al. (1998). "A Novel Role for TGF-β and IL-10 in the Induction of Immune Privilege." The Journal of Immunology, vol. 160, No. 5: 2089-2098.

Dudley, M. E. et al. (2002). "Cancer Regression and Autoimmunity in Patients After Clonal Repopulation with Antitumor Lymphocytes." Science, vol. 298, No. 5594: pp. 850-854.

Egeter, O. et al. (2000). "Eradication of Disseminated Lymphomas with CpG-DNA Activated T Helper Type 1 Cells from Nontransgenic Mice." Cancer Research, vol. 60, No. 6: 1515-1520.

Eibl, B. et al. (1996). "Evidence for a Graft-Versus-Tumor Effect in a Patient Treated With Marrow Ablative Chemotherapy and Allogeneic Bone Marrow Transplantation for Breast Cancer:" Blood, vol. 88, No. 4: pp. 1501-1508.

Elsasser-Beile, U. et al. (1999). "Semiquantitative analysis of Th1 and Th2 cytokine expression in CD3+, CD4+, and CD8+ renal-cell-carcinoma-infiltrating lymphocytes." Cancer Immunol Immunother, vol. 48, No. 4: pp. 204-208.

Emori, Y., H. Sasaki, et al. (1996). "Effect of Z-100, an immunomodulator extracted from human type tubercle bacilli, on the pulmonary metastases of Lewis lung carcinoma in attempt to regulate suppressor T cells and suppressor factor, IL-4." Biotherapy 9(4): 249-56.

Ertl, B., F. Heigl, et al. (2000). "Lectin-mediated bioadhesion: preparation, stability and caco-2 binding of wheat germ agglutinin-functionalized Poly(D,L-lactic-co-glycolic acid)-microspheres." J Drug Targt 8(3): 173-84.

Fan, X. G., W. E. Liu, et al. (1998). "Circulating Th1 and Th2 cytokines in patients with hepatitis C virus infection." Mediators Inflamm 7(4): 295-7.

Finke, J. H., P. Rayman, et al. (1992). "Characterization of a human renal cell carcinoma specific cytotoxic CD8+ T cell line." J Immunother 11(1): 1-11.

Finke, J. H., P. Rayman, et al. (1994). "Characterization of tumor-infiltrating lymphocyte subsets from human renal cell carcinoma: specific reactivity defined by cytotoxicity, interferon-gamma secretion, and proliferation." J Immunother Emphasis Tumor Immunol 15(2): 91-104.

Flanagan, D. L. et al. (1999). "Th1 Cytokines and NK Cells Participate in the Development of Murine Syngeneic Graft-Versus-Host Disease." The Journal of Immunology, vol. 163, No. 3: pp. 1170-1177.

Fowler, D. H., J. Breglio, et al. (1996). "Allospecific CD4+, Th1/Th2 and CD8+, Tc1/Tc2 populations in murine GVL: type I cells generate GVL and type II cells abrogate GVL." Biol Blood Marrow Transplant 2(3): 118-25.

Fowler, D. H. and R. E. Gress (2000). "Th2 and Tc2 cells in the regulation of GVHD, GVL, and graft rejection: considerations for the allogeneic transplantation therapy of leukemia and lymphoma." Leuk Lymphoma 38(3-4): 221-34.

Frassoni, F., M. Labopin, et al. (1996). "Results of allogeneic bone marrow transplantation for acute leukemia have improved in Europe with time—a report of the acute leukemia working party of the European group for blood and marrow transplantation (EBMT)." Bone Marrow Transplant 17(1): 13-8.

Freeman, G. J. et al. (2002). "Protect the killer: CTLs need defenses against the tumor." Nature Medicine, vol. 8, No. 8: pp. 787-789.

Friess, H., H. G. Beger, et al. (1996). "Treatment of advanced pancreatic cancer with mistletoe: results of a pilot trial." Anticancer Res 16(2): 915-20.

Fujimoto, T. et al. (1997). "Streptococcal Preparation OK-432 is a Potent Inducer of IL-12 and a T Helper Cell 1 Dominant State." The Journal of Immunology, vol. 158, No. 12: pp. 5619-5626.

Fulisao, S. et al. (1998). "Th1/Th2 balance alteration in the clinical course of a patient with pure red cell aplasia and thymoma." British Journal of Haematology, vol. 103, No. 2: pp. 308-310.

Gabrilovich, D. I. et al. (1996). "Dendritic Cells in Antitumor Immune Responses. II. Dendritic Cells Grown from Bone Marrow Precursors, but Not Mature DC from Tumor-Bearing Mice, Are Effective Antigen Carriers in the Therapy of Established Tumors." Cellular Immunology, vol. 170, No. 1: pp. 111-119.

(56) References Cited

OTHER PUBLICATIONS

Gale, R. P. et al. (1984). "How Does Bone-Marrow Transplantation Cure Leukaemia?" The Lancet, vol. 2, No. 8393: pp. 28-30.

Garlie, N. K., A.V. LeFever, et al. (1999). "T cells coactivated with immobilized anti-CD3 and anti-CD28 as potential immunotherapy for cancer." J Immunother 22(4): 336-45.

Geppert, T.D. et al. (1988). "Activation of T Lymphocytes by Immobilized Monoclonal Antibodies to CD3, Regulatory Influences of Monoclonal Antibodies to Additional T Cell Surface Determinants." J. Clin. Invest, , vol. 81: pp. 1497-1505.

Ghosh, P., K. L. Komschlies, et al. (1995). "Gradual loss of T-helper 1 populations in spleen of mice during progressive tumor growth." J Natl Cancer Inst 87(19): 1478-83.

Gorelik, L., A. Prokhorova, et al. (1994). "Low-dose melphalan-induced shift in the production of a Th2-type cytokine to a Th1-type cytokine in mice bearing a large MOPC-315 tumor." Cancer Immunol Immunother 39(2): 117-26.

Grakoui, A. et al, (1999). "The Immunological Synapse: A Molecular Machine Controlling T Cell Activation," Science, vol. 285, No. 5425: pp. 221-227.

Granucci, F. et al. (2001). "Transcriptional reprogramming of dendritic cells by differentiation stimuli." Eur J Immunol, vol. 31, No. 9: pp. 2539-2546.

Grigg, A., P. Bardy, et al. (1999). "Fludarabine-based non-myeloablative chemotherapy followed by infusion of HLA-identical stem cells for relapsed leukaemia and lymphoma." Bone Marrow Transplant 23(2): 107-10.

Grohmann, U., M. C. Fioretti, et al. (1998). "Dendritic cells, interleukin 12, and CD4+ lymphocytes in the initiation of class I-restricted reactivity to a tumor/self peptide." Crit Rev Immunol 18(1-2): 87-98.

Hara, I., H. Hotta, et al. (1996). "Rejection of mouse renal cell carcinoma elicited by local secretion of interleukin-2." Jpn J Cancer Res 87(7): 724-9.

Heine, G. et al. (2002). "A shift in the Th(1)/Th(2) ratio accompanies the clinical remission of systemic lupus erythematosus in patients with end-stage renal disease." Nephrology Dialysis Transplantion, vol. 17, No. 10: pp. 1790-1794.

Heniford, B. T. et al. (1994). "Interleukin-8 Suppresses the Toxicity and Antitumor Effect of Interleukin-2." Journal of Surgical Research, vol. 56, No. 1: pp. 82-88.

Herlyn, D. and B. Birebent (1999). "Advances in cancer vaccine development" Ann Med 31(1): 66-78.

Horiguchi, S. et al. (1999). "Primary Chemically Induced Tumors Induce Profound Immunosuppression Concomitant with Apoptosis and Alterations in Signal Transduction in T Cells and NK Cells." Cancer Research, vol. 59, No. 12: pp. 2950-2956.

Inagawa, H., T. Nishizawa, et al. (1998). "Mechanisms by which chemotherapeutic agents augment the antitumor effects of tumor necrosis factor: involvement of the pattern shift of cytokines from Th2 to Th1 in tumor lesions." Anticancer Res 18(5D): 3957-64.

Ito, N. et al. (1999). "Lung Carcinoma: Analysis of T Helper Type 1 and 2 Cells and T Cytotoxic Type 1 and 2 Cells by Intracellular Cytokine Detection with Flow Cytometry." Cancer, vol. 85, No. 11: pp. 2359-2367.

Janes, P. W. et al. (1999). "Aggregation of Lipid Rafts Accompanies Signaling Via the T Cell Antigen Receptor." The Journal of Cell Biology, vol. 147, No. 2: pp. 447-461.

Jung, U. et al. (Nov. 2003). "CD3/CD28-costimulated T1 and T2 subsets: differential in vivo allosensitization generates distinct GVT and GVHD effects." Blood, vol. 1, No. 9: pp. 3439-3446.

Kadowaki, N. et al. (2002). "Natural Type I Interferon-Producing Cells as a Link Between Innate and Adaptive Immunity." Human Immunology, vol. 63, No. 12: pp. 1126-1132.

Kai, S. and H. Hara (2003). "Allogeneic hematopoietic stem cell transplantation." Therap Apher Dial 7(3): 285-91.

Kasakura, S. (1998). "[A role for T-helper type 1 and type 2 cytokines in the pathogenesis of various human diseases]." Rinsho Byori 46(9): 915-21.

Kitahara, S., M. Ikeda, et al. (1996). "Inhibition of head and neck metastatic and/or recurrent cancer by local administration of multi-cytokine inducer OK-432." J Laryngol Otol 110(5): 449-53.

Knoefel, B., K. Nuske, et al. (1997). "Renal cell carcinomas produce IL-6, IL-10, IL-11, and TGF-beta 1 in primary cultures and modulate T lymphocyte blast transformation." J Interferon Cytokine Res 17(2): 95-102.

Kobayashi, M. et al. (1998). "A Pathogenic Role of Th2 Cells and Their Cytokine Products on the Pulmonary Metastasis of Murine B16 Melanoma." The Journal of Immunology, vol. 160, No. 12: pp. 5869-5873.

Kobayashi, M., R. B. Pollard, et al. (1997). "Inhibition of pulmonary metastasis by Z-100, an immunomodulatory lipid-arabinomannan extracted from *Mycobacterium tuberculosis*, in mice inoculated with B16 melanoma." Anticancer Drugs 8(2): 156-63.

Lahn, M. et al. (1999). "Pro-Inflammatory and T Cell Inhibitory Cytokines Are Secreted at High Levels in Tumor Cell Cultures of Human Renal Cell Carcinoma." European Urology, vol. 35, No. 1: pp. 70-80.

Langenkamp, A. et al. (2000). "Kinetics of dendritic cell activation: impact on priming of TH1, TH2 and nonpolarized T cells." Nature Immunology, vol. 1, No. 4: 311-316.

Laux, I. et al. (2000). "Response Differences between Human CD4(+) and CD8(+) T-Cells during CD28 Costimulation: Implications for Immune Cell-Based Therapies and Studies Related to the Expansion of Double-Positive T-Cells during Aging." Clinical Immunology, vol. 96, No. 3: pp. 187-197.

Le Bon, A. et al. (2002). "Links between innate and adaptive immunity via type I interferon." Current Opinion Immunology, vol. 14, No. 4: pp. 432-436.

Lee, P. P. et al. (1997). "T Helper 2-Dominant Antilymphoma Immune Response is Associated With Fatal Outcome." Blood, vol. 90, No. 4: pp. 1611-1617.

Levine, B.L. et al. (1997). "Effects of CD28 Costimulation on Long-Term Proliferation of CD4+ T Cells in the Absence of Exogenous Feeder Cells." The Journal of Immunology, vol. 159, No. 12: pp. 5921-5930.

Li, L. et al. (1998). "Cyclophosphamide Given After Active Specific Immunization Augments Antitumor Immunity by Modulation of Th1 Commitment of CD4+ T Cells." Journal of Surgical Oncology, vol. 67, No. 4: pp. 221-227.

Liebowitz, D.N. et al. (1998). "Costimulatory approaches to adoptive immunotherapy." Current Opinion Oncology, vol. 10, No. 6: pp. 533-541.

Lowes, M. A., G. A. Bishop, et al. (1997). "T helper 1 cytokine mRNA is increased in spontaneously regressing primary melanomas." J Invest Dermatol 108(6): 914-9.

Ludviksson, B. R. et al. (2000). "The effect of TGF-$\beta$1 on immune responses of naive versus memory CD4+ Th1/Th2 T cells." Eur J Immunol, vol. 30, No. 7: pp. 2101-2111.

Lum, L.G. et al (2001). "Immune modulation in cancer patients after adoptive transfer of ani-CD3/anti-CD28-costimulated T-cells—phase I clinical trial." Journal of Immunotherapy, vol. 24, No. 5: pp. 408-419.

Ma, J. at al. (1998). "Use of encapsulated single chain antibodies for induction of anti-idiotypic humoral and cellular immune responses." Journal of Pharmaceutical Sciences, Vo. 87, No. 11: pp. 1375-1378.

Maeurer, M. J., D. M. Martin, et al. (1995). "Host immune response in renal cell cancer: interleukin-4 (IL-4) and IL-10 mRNA are frequently detected in freshly collected tumor-infiltrating lymphocytes." Cancer Immunol Immunother 41(2): 111-21.

Maus, M. V. et al. (2002). "Ex vivo expansion of polyclonal and antigen-specific cytotoxic T lymphocytes by artificial APCs expressing ligands for the T-cell receptor, CD28 and 4-1BB." Nature Biotechnology, vol. 20, No. 2: pp. 143-148.

Menetrier-Caux, C. et al. (1999). "Renal cell carcinoma induces interleukin 10 and prostaglandin E2 production by monocytes." British Journal of Cancer, vol. 79, No. 1: pp. 119-130.

Moran, M. et al. (1998). "Engagement of GPI-Linked CD48 Contributes to TCR Signals and Cytoskeletal Reorganization: A Role for Lipid Rafts in T Cell Activation." Immunity, vol. 9, No. 6: pp. 787-796.

(56) References Cited

OTHER PUBLICATIONS

Muller, M. at al. (2003). "Surface modification of PLGA microspheres." Journal of Biomedic Material Research, vol. 66A,No. 1: pp. 55-61.
Nabioullin, R. et al. (1994). "Interleukin-10 is a potent inhibitor of tumor cytotoxicity by human monocytes and alveolar macrophages." Journal of Leukocyte Biology, vol. 55, No. 4: pp. 437-442.
Nakagomi, H. et al. (1995). "Lack of Interleukin-2 (IL-2) Expression and Selective Expression of IL-10 mRNA in Human Renal Cell Carcinoma." Int. Journal of Cancer, vol. 63, No. 3: pp. 366-371.
Nishimura, T. et al. (2000). "The critical role of Th1-dominant immunity in tumor immunology." Cancer Chemother Pharmacol, vol. 46 (Suppl): S52-S61.
Nitta, T., M. Hishii, et al. (1994). "Selective expression of interleukin-10 gene within glioblastoma multiforme." Brain Res 649(1-2): 122-8.
O'Donnell P.B. et al. (1997). "Preparation of microspheres by the solvent evaporation technique." Advanced Drug Delivery Reviews, vol. 28, No. 1: pp. 25-42.
Oka, H. et al. (1999). "An immunomodulatory arabinomannan extracted from Mycobacterium tuberculosis, Z-100, restores the balance of Th1/Th2 cell responses in tumor bearing mice." Immunology Letters, vol. 70, No. 2: pp. 109-117.
Okamoto, T. et al. (1997). "Local Injection of OK432 Can Augment the TH1-Type T-Cell Response in Tumor-Draining Lymph Node Cells and Increase Their Immunotherapeutical Potential." International Journal of Cancer, vol. 70, No. 5: pp. 598-605.
Okutomi, T., Y. Kato, et al. (2000). "[Clinical effects of adjuvant therapy using Z-100 (Ancer 20 injection) for oral cancer—prevention of stomatitis and hematopoietic impairment]." Gan To Kagaku Ryoho 27(1): 65-71.
Onishi, T. et al. (1999). "An assessment of the immunological environment based on intratumoral cytokine production in renal cell carcinoma." BJU International, vol. 83, No. 4: pp. 488-492.
Raghupathy, R. (1997). "Th1-type immunity is incompatible with successful pregnancy." Immunology Today, vol. 18, No. 10: pp. 478-482.
Raghupathy, R. et al. (1999). "Maternal Th1- and Th2-Type Reactivity to Placental Antigens in Normal Human Pregnancy and Unexplained Recurrent Spontaneous Abortions." Cellular Immunology, vol. 196, No. 2: pp. 122-130.
Rondon, G., S. Giralt, et al. (1996). "Graft-versus-leukemia effect after allogeneic bone marrow transplantation for chronic lymphocytic leukemia." Bone Marrow Transplant 18(3): 669-72.
Rosenberg, S. A. (2001). "Progress in the development of immunotherapy for the treatment of patients with cancer." Journal of Internal Medicine, vol. 250, No. 6: pp. 462-475.
Roussel, E. et al. (1996). "Predominance of a type 2 intratumoural immune response in fresh tumour-infiltrating lymphocytes from human gliomas." Clinical and Experimental Immunology, vol. 105, No. 2: pp. 344-352.
Rubbi, C.P. et al. (1993). "Evidence of surface antigen detachment during incubation of cells with immunomagnetic beads." Journal of Immunology Methods, vol. 166, No. 2: pp. 233-241.
Santin, A. D. et al. (2000). "Interleukin-10 Increases Th1 Cytokine Production and Cytotoxic Potential in Human Papillomavirus-Specific CD8(+) Cytotoxic T-Lymphocytes." Journal of Virology, vol. 74, No. 10: pp. 4729-4737.
Sato, M., S. Goto, et al. (1998). "Impaired production of Th1 cytokines and increased frequency of Th2 subsets in PBMC from advanced cancer patients." Anticancer Res 18(5D): 3951-5.
Saxton, M. L. et al. (1997). "Adoptive Transfer of Anti-CD3-Activated CD4+ T Cells Plus Cyclophosphamide and Liposome-Encapsulated Interleukin-2 Cure Murine MC-38 and 3LL Tumors and Establish Tumor-Specific Immunity," Blood, vol. 89, No. 7: pp. 2529-2536.
Shibuya, T.Y. et al. (2000). "Anti-CD3/Anti-CD28 Bead Stimulation Overcomes CD3 Unresponsiveness in Patients With Head and Neck Squamous Cell Carcinoma." Arch Otolaryngol Head Neck Surg, vol. 126, No. 4: 473-479.

Shinomiya, Y., M. Harada, et al. (1995), "Anti-metastatic activity induced by the in vivo activation of purified protein derivative (PPD)-recognizing Th1 type CD4+ T cells." Immunobiology 193(5): 439-55.
Shurin, M. R., L. Lu, et al. (1999). "Th1/Th2 balance in cancer, transplantation and pregnancy." Springer Semin Immunopathol 21(3): 339-59.
Slavin, S. et al. (2001). "Non-myeloablative allogeneic Stem cell transplantation focusing on immunotherapy of life-threatening malignant and non-malignant diseases." Critical Reviews Oncology Hematology, vol. 39, No. 1-2: pp. 25-29.
Slavin, S. at al. (1995). "Allogeneic cell therapy for relapsed leukemia after bone marrow transplantation with donor peripheral blood lymphocytes." Experimental Hematology, vol. 23, No. 14: pp. 1553-1562.
Slavin, S. et al. (1996). "Allogeneic Cell Therapy With Donor Peripheral Blood Cells and Recombinant Human Interleukin-2 to Treat Leukemia Relapse After Allogeneic Bone Marrow Transplantation." Blood, vol. 87, No. 6: pp. 2195-1204.
Slavin, S. et al. (1996). "Allogeneic Cell Therapy: the Treatment of Choice for All Hematologic Malignancies Relapsing Post BMT." Blood, vol. 87, No. 9: pp. 4011-4013.
Slavin, S. et al. (2001). "Nonmyeloablative stem cell transplantation for the treatment of cancer and life-threatening nonmalignant disorders: past accomplishments and future goals." Cancer Chemother Pharmacol, vol. 48, (Suppl 1): pp. S79-S84.
Slavin, S. et al. (1998). "Immunotherapy in conjunction with autologous and allogeneic blood or marrow transplantation in lymphoma." Annals of Oncology, vol. 9 (Suppl 1): pp. S31-S39.
Smith, D. R., S. L. Kunkel, et al. (1994). "Production of interleukin-10 by human bronchogenic carcinoma." Am J Pathol 145(1): 18-25.
Smyth, M. J. et al. (2002). "New Aspects of Natural-Killer-Cell Surveillance and Therapy of Cancer." Nature Reviews Cancer, vol. 2, No. 11: pp. 850-861.
Sredni, B. et al. (1995). "Bone Marrow-Sparing and Prevention of Alopecia by AS101 in Non-Small-Cell Lung Cancer Patients Treated with Carboplatin and Etoposide." Journal of Clinical Oncology, vol. 13, No. 9: pp. 2342-2353.
Sredni, B. et al. (1996). "Predominance of TH1 Response in Tumor-Bearing Mice and Cancer Patients Treated with AS101." National Journal of Cancer Institute, vol. 88, No. 18: pp. 1276-1284.
Sredni, B., R. H. Xu, et al. (1996). "The protective role of the immunomodulator AS101 against chemotherapy-induced alopecia studies on human and animal models." Int J Cancer 65(1): 97-103.
Stein, G., W. Henn, et al. (1998). "Modulation of the cellular and humoral immune responses of tumor patients by mistletoe therapy." Eur J Med Res 3(4): 194-202.
Stern, B. V. et al. (2002). "Vaccination with Tumor Peptide in CpG Adjuvant Protects Via IFN-Gamma-Dependent CD4 Cell Immunity." The Journal of Immunology, vol. 168, No. 12: pp. 6099-6105.
Tabata, T. et al. (1999). "Th2 Subset Dominance Among Peripheral Blood T Lymphocytes in Patients with Digestive Cancers." American Journal of Surgery, vol. 177, No. 3: pp. 203-208.
Taga, K. et al. (1993). "Human Interleukin-10 Can Directly Inhibit T-Cell Growth." Blood, vol. 81, No. 11: pp. 2964-2971.
Takeuchi, T. et al. (1997). "Th2-like response and antitumor effect of anti-interleukin-4 mAb in mice bearing renal cell carcinoma." Cancer Immunol Immunother, vol. 43, No. 6: pp. 375-381.
Tanaka, K., K. Kemmotsu, et al. (1998). "[Flow cytometric analysis of helper T cell subsets (Th1 and Th2) in healthy adults]." Rinsho Byori 46(12): 1247-51.
Tanaka, J., M. Imamura, et al. (1997). "The important balance between cytokines derived from type 1 and type 2 helper T cells in the control of graft-versus-host disease." Bone Marrow Transplant 19(6): 571-6.
Tatsumi, T. et al. (2002). "Disease-associated bias in T helper type 1 (Th1)/Th2 CD4(+) T cell responses against MAGE-6 in HLA-DRB10401(+) patients with renal cell carcinoma or melanoma." Journal of Experimental Medicine, vol. 196, No. 5: pp. 619-628.
Terao, H., M. Harada, et al. (1994). "Th1 type CD4+ T cells may be a potent effector against poorly immunogenic syngeneic tumors." Biotherapy 8(2): 143-51.

(56) References Cited

OTHER PUBLICATIONS

Tessmar, J. et al. (2003). "The use of poly(ethylene glycol)-block-poly(lactic acid) derived copolymers for the rapid creation of biomimetic surfaces." Biomaterials, vol. 24, No. 24: pp. 4475-4486.

Thanhauser, A., A. Bohle, et al. (1995). "The induction of bacillus-Calmette-Guerin-activated killer cells requires the presence of monocytes and T-helper type-1 cells." Cancer Immunol Immunother 40(2): 103-8.

Thomas, A. K. et al. (2002). "A Cell-Based Artificial Antigen-Presenting Cell Coated with Anti-CD3 and CD28 Antibodies Enables Rapid Expansion and Long-Term Growth of CD4 T Lymphocytes." Clinical Immunology, vol. 105, No. 3: pp. 259-272.

Thomas, E., R. Storb, et al. (1975). "Bone-marrow transplantation (first of two parts)." N. Engl J Med 292(16): 832-43.

Thomas, E. D., R. Storb, et al. (1975). "Bone-marrow transplantation (second of two parts)." N Engl J Med 292(17): 895-902.

Tilg, H. et al. (1994). "Interleukin-6 (IL-6) as an Anti-inflammatory Cytokine: Induction of Circulating IL-1 Receptor Antagonist and Soluble Tumor Necrosis Factor Receptor p55." Blood, vol. 83, No. 1: pp. 113-118.

To, W. C. et al. (2000). "Therapeutic Efficacy of Th1 and Th2 L-selectin—CD4+ Tumor-Reactive T Cells." Laryngoscope vol. 110, (10 Pt 1): pp. 1648-1654.

Ueno, N. T., G. Rondon, et al. (1998). "Allogeneic peripheral-blood progenitor-cell transplantation for poor-risk patients with metastatic breast cancer." J Clin Oncol 16(3): 986-93.

van Besien, K., P. Thall, et al. (1997). "Allogeneic transplantation for recurrent or refractory non-Hodgkin's lymphoma with poor prognostic features after conditioning with thiotepa, busulfan, and cyclophosphamide: experience in 44 consecutive patients." Biol Blood Marrow Transplant 3(3): 150-6.

Voutsadakis, I. A. (2003). "NK cells in allogeneic bone marrow transplantation." Cancer Immunol Immunother, vol. 52, No. 9: pp. 525-534.

Vowels, B. R. et al. (1994). "Th2 Cytokine mRNA Expression in Skin in Cutaneous T-Cell Lymphoma." The Journal of Investigative Dermatology, vol. 103, No. 5: pp. 669-673.

Wang, Q. et al. (1995). "Selective Cytokine Gene Expression in Renal Cell Carcinoma Tumor Cells and Tumor-Infiltrating Lymphocytes." International Journal of Cancer, vol. 61, No. 6: pp. 780-785.

Weber, K., U. Mengs, et al. (1998). "Effects of a standardized mistletoe preparation on metastatic B16 melanoma colonization in murine lungs." Arzneimittelforschung 48(5): 497-502.

Weiden, P. L. et al. (1981). "Antileukemic Effect of Chronic Graft-Versus-Host Disease: Contribution to Improved Survival After Allogeneic Marrow Transplantation." New England Journal of Medicine, vol. 304 No. 25: pp. 1529-1533.

Whitmore, M. et al. (1999). "LPD lipopolyplex initiates a potent cytokine response and inhibits tumor growth." Gene Therapy, vol. 6, No. 11: pp. 1867-1875.

Wong B. R. et al. (1999). "TRANCE is a TNF family member that regulates dendritic cell and osteoclast function." Journal of Leukocyte Biology, vol. 65, No. 6: pp. 715-724.

Woo, E. Y. et al. (2001). "Regulatory CD4(+)CD25(+) T Cells in Tumors from Patients with Early-Stage Non-Small Cell Lung Cancer and Late-Stage Ovarian Cancer." Cancer Research, vol. 61, No. 12: pp. 4766-4772.

Woo, E. Y. et al. (2002). "Cutting edge: Regulatory T Cells from Lung Cancer Patients Directly Inhibit Autologous T cell proliferation," J Immunol 168(9): 4272-6.

Yamamura, M. (1992). "Defining protective responses to pathogens: cytokine profiles in leprosy lesions." Science 255 (5040): 12.

METHOD TO FORMULATE T-CELLS

CROSS-REFERENCE TO RELATED APPLICATION

The present application is a continuation of and claims priority of U.S. patent application Ser. No. 12/173,330 filed Jul. 15, 2008 which is a divisional of U.S. patent application Ser. No. 11/069,010, filed Mar. 1, 2005, now U.S. Pat. No. 7,402,431 which is a continuation-in-part of patent application Ser. No. 10/838,454, filed May 4, 2004, now U.S. Pat. No. 7,435,592, which also claims priority of U.S. provisional patent application Ser. Nos. 60/549,032, filed Mar. 1, 2004, 60/547,966, filed Feb. 26, 2006, 60/545,450, filed Feb. 18, 2004 and 60/470,171, filed May 13, 2003, the content of which is hereby incorporated by reference in its entirety.

FIELD OF INVENTION

This invention relates to methods for formulating ex-vivo prepared T-cells for infusion.

BACKGROUND OF THE INVENTION

Cell therapy methods have been developed in order to enhance the host immune response to tumors, viruses and bacterial pathogens. Cell therapy methods often involve the ex-vivo activation and expansion of T-cells. Examples of these type of treatments include the use of tumor infiltrating lymphocyte (TIL) cells (see U.S. Pat. No. 5,126,132 issued to Rosenberg), cytotoxic T-cells (see U.S. Pat. No. 6,255,073 issued to Cai, et al.; and U.S. Pat. No. 5,846,827 issued to Celis, et al.), expanded tumor draining lymph node cells (see U.S. Pat. No. 6,251,385 issued to Terman), and various other lymphocyte preparations (see U.S. Pat. No. 6,194,207 issued to Bell, et al.; U.S. Pat. No. 5,443,983 issued to Ochoa, et al.; U.S. Pat. No. 6,040,177 issued to Riddell, et al.; U.S. Pat. No. 5,766,920 issued to Babbitt, et al.).

For maximum effectiveness of T-cells in cell therapy protocols, the ex vivo activated T-cell population should be in a state of maximal activation upon infusion. Efforts for developing improved methods for producing more effective T-cells for use in cell therapy protocols have focused on the ex-vivo activation methods. However, ex-vivo activated cells need to be harvested and administered to patients to have a therapeutic effect. The harvesting of the T-cells removes them from the activating stimuli available in the ex-vivo cultures. Therefore, the longer the time from harvest to infusion, the lower the quality of the T-cells.

There is a need to develop T-cell formulations for infusion that maintain the cells in a state that can maximally orchestrate an immune response to cancer, infectious diseases and other disease states at both the time of infusion and while circulating in the blood. Efforts to maintain the activation state of T-cells at the time of infusion have most commonly involved the formulation of the T-cells with exogenous IL-2. Systemic IL-2 administration to patients has also been used to maintain the activation state of T-cells post-infusion. However, exogenous IL-2 administration is extremely toxic to patients and has not resulted in significant benefit to patients undergoing T-cell infusions.

SUMMARY OF THE INVENTION

This disclosure includes a method for formulating T-cells for use as a medicant comprising activating the T-cells by incubating the T-cells in a nutrient culture media with an activating agent. The T-cells together with the activating agent are suspended in a media suitable for infusion. The activated T-cells are packaged together with the activating agent in a container suitable for administration to a patient.

For the purposes of the present invention, all references to T-cells includes a population of cells with at least a portion of the cells containing T-cells. T-cells are cells which express TCR, including $\alpha/\beta$ and $\gamma/\delta$ TCRs. T-cells include all cells which express CD3, including T-cell subsets which also express CD4 and CD8. T-cells include both naïve and memory cells and effector cells such as CTL. T-cells also include regulatory cells such as Th1, Tc1, Th2, Tc2, Th3, Treg, and Tr1 cells. T-cells also include NKT-cells and similar unique classes of the T-cell lineage.

PREFERRED EMBODIMENTS

The biodegradable spheres of the present invention are preferably manufactured from aliphatic polyesters, such as poly(lactic acid) (PLA), poly(glycolic acid) (PGA), copolymers of PLA and PGA (PLGA) or poly(carprolactone) (PCL), and polyanhydrides. The spheres are produced into small particle sizes of 0.1 to 500 microns, preferably less than 10 microns and most preferably less than 1 micron. Microspheres of this size range are capable of direct injection into the body by conventional methods. It is preferred that the coated spheres be designed to degrade in physiological fluids within 7 days, more preferably within 3 days.

The preferred first material for coating on the biodegradable spheres is polyclonal goat (or sheep) anti-mouse polyclonal antibodies. By way of example, this preferred first material can be used to cross-link mouse-derived monoclonal antibodies, or fragments or genetically engineered derivatives thereof, that have specificity for T-cell surface moieties. Thus, for example, the mixing of goat anti-mouse coated microspheres (or nanospheres) with human T-cells labeled with mouse anti-human CD3 and mouse anti-human CD28 mAbs will cause the cross-linking of the mouse mAbs on the human T-cells through the binding of the goat anti-mouse polyclonal antibody with the mouse mAbs. The cross-linking of the mAbs causes the activation of the T-cells. Alternatively, the anti-human CD3 and anti-CD28 can also be first bound, preferably in a 50/50 ratio, on the goat (or sheep) polyclonal antibody coated spheres and mixed with the T-cells. It will be obvious to those skilled in the art that many combinations of first materials and second materials can be used to accomplish the objective of cross-linking second agents attached to T-cell surface moieties in order to initiate signal transduction and activation of T-cells.

The mixture of T-cells with cross-linked surface moieties is suspended in infusion medium (e.g., isotonic solutions such as normal saline, 5% dextrose, Plasma-Lyte (Baxter) or Normasol (Abbott). In some embodiments, the infusion medium is supplemented with 0.5%-10% human serum albumen (HSA).

The mixture is preferably adjusted to a final T-cell concentration of between $1 \times 10^7$ to $1 \times 10^8$ cells per ml of infusion media. In a preferred embodiment, $10^9$ T-cells are formulated in 100 ml of infusion media. The formulation is then packaged in one or more containers, such as syringes, plastic pouches, or plastic bottles.

Although the present invention has been described with reference to preferred embodiments, workers skilled in the art will recognize that changes may be made in form and detail without departing from the spirit and scope of the invention.

What is claimed is:

1. A method to formulate T-cells for use as a medicant comprising:
   activating the T-cells by incubating the T-cells in a nutrient culture media with an activating agent;
   suspending the activated T-cells together with the activating agent in a media suitable for infusion; and
   packaging the activated T-cells together with the activating agent in a container suitable for administration to a patient.

2. The method of claim 1 wherein the T-cells are Th1 cells.

3. The method of claim 1 wherein the media suitable for infusion is PlasmaLyteA supplemented with human serum albumin.

4. The method of claim 1 wherein the container is a syringe.

* * * * *